United States Patent
Fernandez et al.

(10) Patent No.: US 8,454,501 B2
(45) Date of Patent: Jun. 4, 2013

(54) PROTECTION FOR ENDOSCOPE, AND CORRESPONDING ENDOSCOPE

(75) Inventors: Henri Fernandez, Larra (FR); Nicolas Roddier, Escalquens (FR); Lin Brunel, Blagnac (FR)

(73) Assignee: V.I.M.S. Video Interventionnelle Medicale Scientifique, L'Union (FR)

( * ) Notice: Subject to any disclaimer, the term of this patent is extended or adjusted under 35 U.S.C. 154(b) by 621 days.

(21) Appl. No.: 12/295,726

(22) PCT Filed: Apr. 3, 2007

(86) PCT No.: PCT/FR2007/000564
§ 371 (c)(1),
(2), (4) Date: Apr. 2, 2009

(87) PCT Pub. No.: WO2007/113400
PCT Pub. Date: Oct. 11, 2007

(65) Prior Publication Data
US 2009/0253962 A1    Oct. 8, 2009

(30) Foreign Application Priority Data
Apr. 3, 2006  (FR) ...................... 06 02887

(51) Int. Cl.
*A61B 1/00*  (2006.01)
*A61B 6/00*  (2006.01)
*A61B 1/04*  (2006.01)
*G02B 5/04*  (2006.01)
*G02B 5/08*  (2006.01)

(52) U.S. Cl.
USPC ........... 600/182; 600/478; 600/121; 359/831; 359/838

(58) Field of Classification Search
USPC ................. 600/182, 473, 478, 116, 121, 178, 600/102, 101, 173, 160; 137/560; 359/831, 359/838; 348/45, 65
See application file for complete search history.

(56) References Cited

U.S. PATENT DOCUMENTS

| 216,618 | A | * | 6/1879 | Arai ............................ 24/182 |
| 3,801,181 | A | * | 4/1974 | Kitano et al. ............... 359/652 |

(Continued)

FOREIGN PATENT DOCUMENTS

| CN | 1217637 A | 5/1999 |
| EP | 0 211 976 A1 | 3/1987 |

(Continued)

OTHER PUBLICATIONS

Chinese Office Action dated May 12, 2010 in Corresponding Application 200780019086.0.

(Continued)

*Primary Examiner* — Anhtuan Nguyen
*Assistant Examiner* — Ronald D Colque
(74) *Attorney, Agent, or Firm* — Young & Thompson

(57) ABSTRACT

This protection for an endoscope includes a sheath with a rigid cylindrical tubular part (8), and an associated flexible sleeve. The rigid cylindrical tubular part (8) is made of a material permitting transport of light. The rigid cylindrical tubular part (8) is treated in such a way as to guide the light from a light source at its proximal end (10) to its distal end (12). The distal end (12) of the cylindrical tubular part (8) has elements (14, 16) for diffusing and/or orienting the light guided via the cylindrical tubular part (8). The endoscope is designed to use a protection in order to illuminate the cavity to be examined in the patient's body.

5 Claims, 4 Drawing Sheets

U.S. PATENT DOCUMENTS

Figure 1:
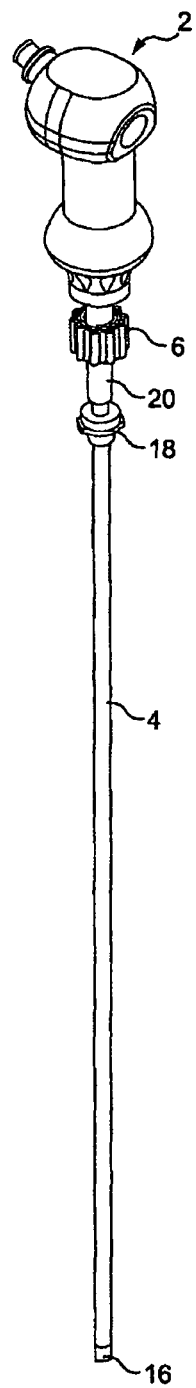

| | | | | |
|---|---|---|---|---|
| 4,878,485 | A | * 11/1989 | Adair | 600/122 |
| 5,377,047 | A | * 12/1994 | Broome et al. | 359/654 |
| 5,704,892 | A | * 1/1998 | Adair | 600/121 |
| 6,124,883 | A | * 9/2000 | Suzuki et al. | 348/68 |
| 6,293,910 | B1 | * 9/2001 | Yamakita et al. | 600/132 |
| 6,569,088 | B2 | * 5/2003 | Koshikawa | 600/177 |
| 7,510,524 | B2 | * 3/2009 | Vayser et al. | 600/178 |
| 2003/0216618 | A1 | 11/2003 | Arai | |
| 2004/0036975 | A1 | * 2/2004 | Slatkine | 359/584 |
| 2004/0204651 | A1 | * 10/2004 | Freeman et al. | 600/473 |
| 2005/0215987 | A1 | * 9/2005 | Slatkine | 606/9 |
| 2005/0245789 | A1 | * 11/2005 | Smith et al. | 600/159 |
| 2005/0283048 | A1 | * 12/2005 | Gill et al. | 600/121 |
| 2007/0270653 | A1 | * 11/2007 | Vayser et al. | 600/182 |

FOREIGN PATENT DOCUMENTS

| | | |
|---|---|---|
| EP | 0 456 761 | 8/1990 |
| EP | 0 904 725 A1 | 3/1999 |
| RU | 2192029 C1 | 10/2002 |

OTHER PUBLICATIONS

Khatsevich T.N. "Les endescopes", Manuel, Novosibirsk, SGGA, 2002.

Decision on Grant, dated Jun. 15, 2011, in Application No. 2008143339.

* cited by examiner

PROTECTION FOR ENDOSCOPE, AND CORRESPONDING ENDOSCOPE

BACKGROUND OF THE INVENTION

1. Field of the Invention

The present invention concerns a protection device for endoscopes and a corresponding endoscope.

2. Description of the Related Art

An endoscope is an instrument used in medicine that includes an optical system for examining the internal surface of a hollow organ, a natural cavity or a conduit of the body for diagnostic or therapeutic purposes. Such instruments include an invasive part called the endoscope stem, that penetrates into the body of the patient, and associated means for seeing inside the body of the patient, such as an eyepiece, for example. A light source for illuminating the surface to be observed is generally also associated with the endoscope.

A rigid endoscope, with which the present document is concerned, has a rigid invasive part, as opposed to flexible endoscopes which are sometimes also referred to as fiberscopes. The invasive part of a rigid endoscope usually has a circular cylindrical shape with a diameter of 8 mm, for example. It includes a cylindrical tubular metal envelope containing on the one hand optical lenses for observing via an eyepiece or the like the internal surface of the body to be examined and on the other hand optical fibers for conducting light from an external light source to illuminate the surface to be examined.

The endoscope can be associated with an image capture device, such as a video camera, for example. The resulting instrument is known as a video endoscope.

To avoid any contamination, it is known to sterilize endoscopes before each use. This sterilization is effected in an autoclave. Sterilization of an endoscope takes a long time and the severe conditions under which sterilization is effected damage the endoscope in the long term.

The patent EP-0 456 761 proposes a sterile sheath associated with an accordion-fold sleeve to cover a video endoscope and thereby to avoid having to sterilize it. The sheath protects the invasive part of the endoscope and the sleeve is intended to cover the exterior part of the video endoscope. The use of such sheaths and such sleeves solves the problems associated with sterilizing an endoscope. However the sheath covering the invasive part of the endoscope increases the total diameter of the assembly to be introduced into the body of the patient.

SUMMARY OF THE INVENTION

The aim of the present invention is to solve this problem. Thus the aim of the invention is to provide means for producing an assembly comprising an invasive part including a sterile protection sheath of small outside diameter, preferably the same diameter as the invasive part of an endoscope, that can be sterilized and used with no protective sheath.

To this end, the present invention proposes an endoscope protection device including a sheath with a rigid cylindrical tubular part and an associated flexible sleeve.

According to the invention the rigid cylindrical tubular part is produced in a material able to transport light, the rigid cylindrical tubular part is treated to guide light from a light source from its proximal end to its distal end and the distal end of the cylindrical tubular part includes means for diffusing and/or orienting light guided by the cylindrical tubular part.

Whereas prior art protection devices have only a passive role, a protection device of the invention can have an active role vis à vis the endoscope that it protects by conducting light to the area in the body of a patient to be examined by means of the endoscope. It is then unnecessary to provide in the endoscope means for guiding light from its proximal end to its distal end and the endoscope can therefore have a rigid invasive part of smaller diameter, intended only to transport the image to be observed from the distal end to the proximal end. Overall, the outside diameter of a cylindrical tubular part of a protection device of the invention is substantially identical to that of the invasive part of a prior art endoscope with no protective sheath.

To guide light in the cylindrical tubular part, the latter part includes, for example, a core produced in a first material and the core of this cylindrical tubular part has its interior and exterior faces coated with a material having a refractive index lower than that of the first material. In an embodiment of this kind the material used to produce the core of the cylindrical tubular part is PMMA (polymethylmethacrylate) or a polystyrene, for example, and the coatings are produced in a fluorinated polymer, for example.

In an endoscope protection device of the invention, the means for diffusing and/or orienting light include a diffusion spacer and an angular correction lens, for example. In a preferred embodiment achieving good diffusion of light from the cylindrical tubular part, the diffusion spacer is a tubular part having a plane transverse face adapted to rest against the distal end of the cylindrical tubular part while the face opposite the transverse face has a number of edges, possibly rounded edges, to form a number of prisms. This diffusion spacer can be disposed between the angular correction lens and the distal end of the cylindrical tubular part and there can be a gap between the diffusion spacer and the angular correction lens forming an air lens between those two components. Such air lenses also contribute to good diffusion of light.

The present invention also concerns an endoscope protection device as described above wherein the outside diameter of the rigid tubular part is less than 5 mm.

The present invention also concerns an endoscope including an invasive part having a proximal end and a distal end.

According to the invention, the invasive part includes on the one hand a rigid stem with means for transporting an image from its distal part to its proximal part and on the other hand a protection device as described above and the endoscope further includes a light output for forming, with the aid of illumination means, an annular light beam around the proximal end of the rigid stem and fixing means for receiving the protection device.

One embodiment of this kind of endoscope is a video endoscope and includes a housing in which there are an image sensor and an optical lens assembly associated with the image sensor and the image sensor is mounted coaxially with a conical light guide disposed in front of the optical lens assembly to direct light from external illumination means to produce the annular light beam.

In a preferred embodiment of an endoscope of the invention, the rigid stem consists of an external metal tube inside which is disposed an optical rod for transmitting an image from the distal end of the stem to its proximal end.

BRIEF DESCRIPTION OF THE DRAWING FIGURES

Figure 2:
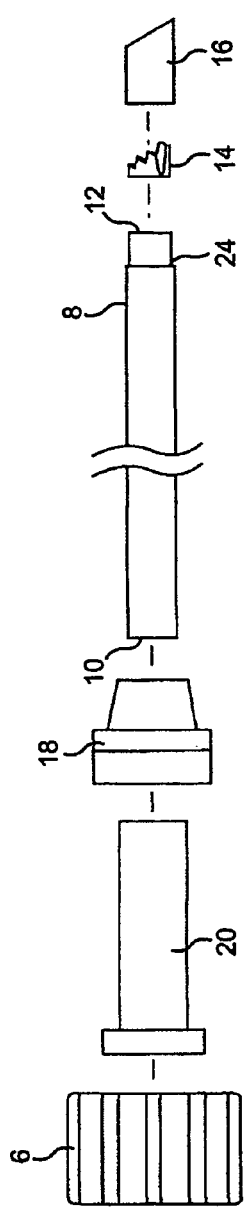
Figure 3:
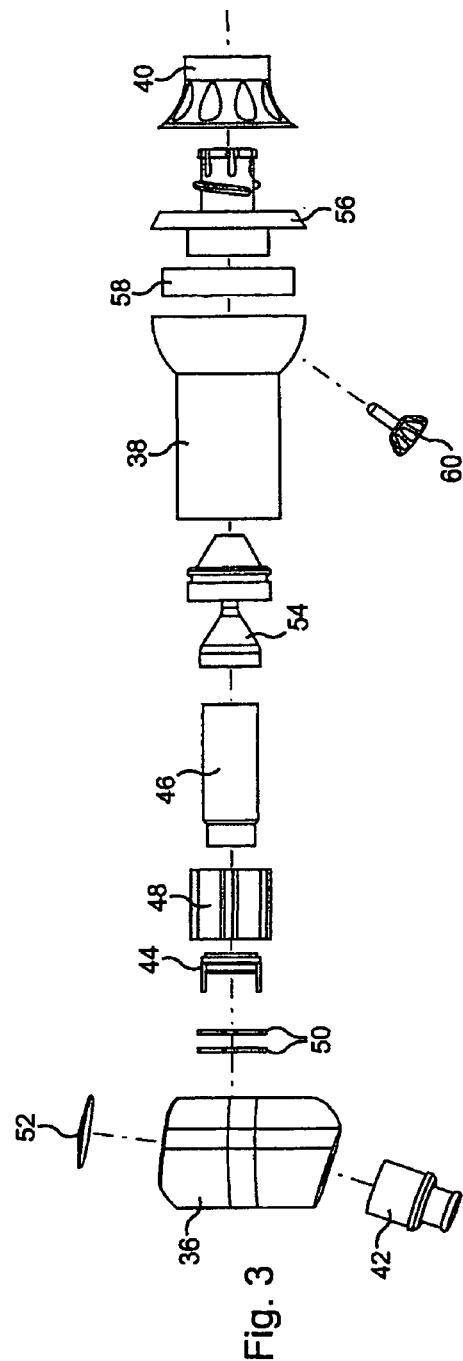
Figure 5:
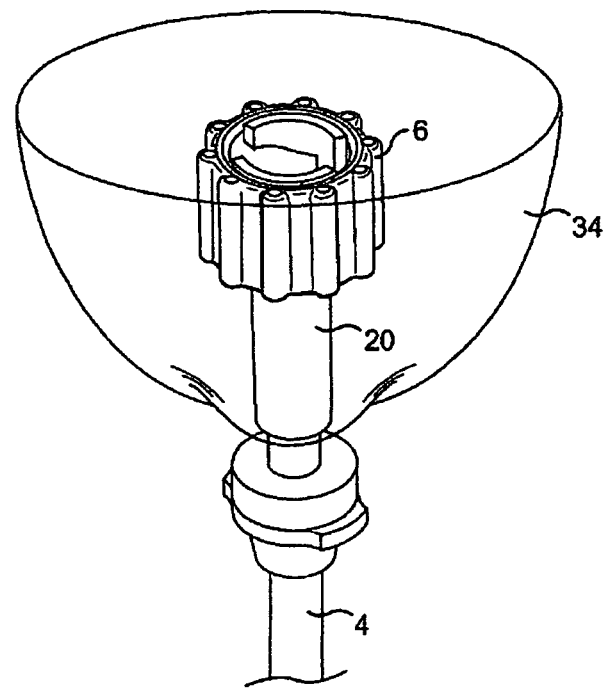
Figure 4:
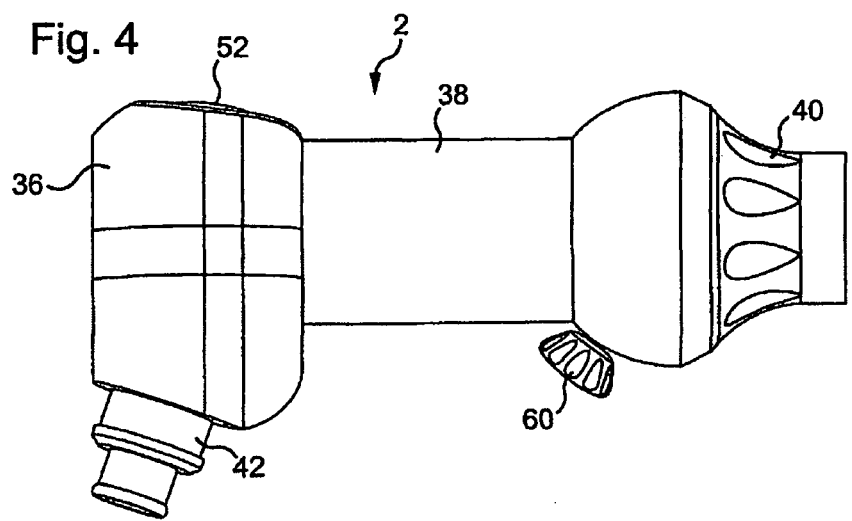
Figure 6:
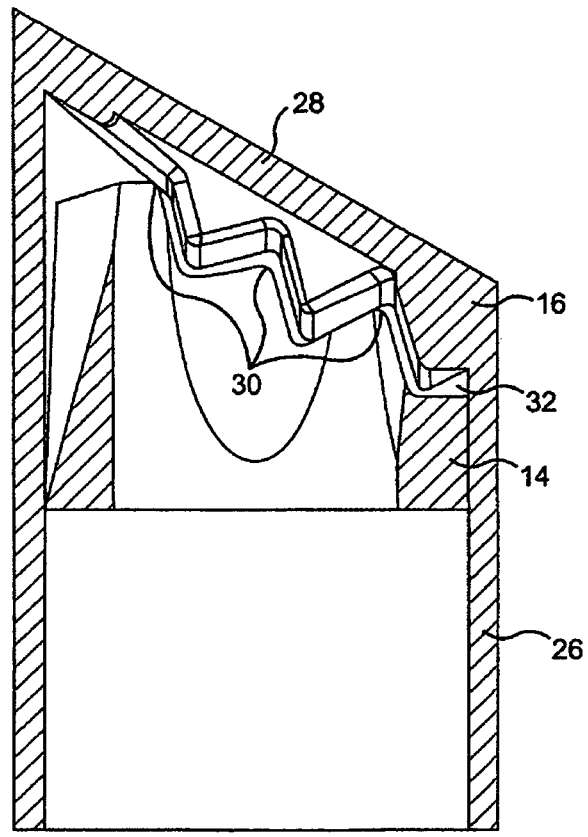
Figure 7:
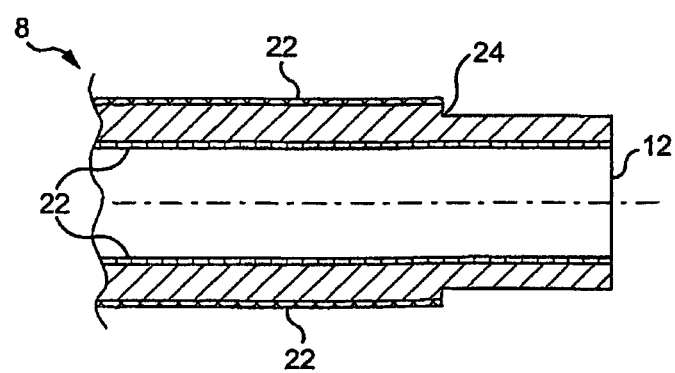

Details and advantages of the present invention will emerge more clearly from the following description, given with reference to the appended diagrammatic drawings, in which:

FIG. 1 is a general view of a video endoscope and a sheath of the invention, the sheath shown in this figure having no flexible sleeve, FIG. 2 is an exploded view of a sheath of the invention without its sleeve, FIG. 3 is an exploded view of the body of a video endoscope of the invention, FIG. 4 shows the body of the video endoscope when assembled, FIG. 5 shows the fixing of a sleeve to a sheath of the invention, FIG. 6 is a view to a larger scale of one embodiment of means for diffusing and orienting light at the end of the sheath of FIG. 2, and FIG. 7 is a partial view in longitudinal section of a rigid part of a sheath of the invention.

DETAILED DESCRIPTION OF THE INVENTION

FIG. 1 shows a video endoscope including an invasive part formed of a rigid optical stem (not visible) covered by a protective sheath 4 fixed to the endoscope by locking means 6.

FIG. 2 shows the protective sheath 4 in more detail. It includes firstly a cylindrical tubular part 8. This has a proximal end 10 and a distal end 12. At the distal end, the protective sheath 4 includes a diffusion spacer 14 and an angular correction lens 16. At the proximal end 10, the protective sheath 4 includes a locking system 18, a sleeve support 20 and locking means 6.

FIG. 7 shows the cylindrical tubular part 8 of the protective sheath 4 in more detail. This figure is a view in longitudinal section of the distal end of this cylindrical tubular part 8. The core of this cylindrical tubular part 8 is made of polycarbonate, for example, PMMA (polymethylmethacrylate), for example. The interior face and the exterior face of this core are covered with a layer 22 of a material having a refractive index lower than that of the material of the core of the cylindrical tubular part 8, for example a fluorinated polymer. These layers 22 can be co-extruded with the core during manufacture of the cylindrical tubular part 8 or deposited on and in the core of the cylindrical tubular part 8.

The distal end 12 of the cylindrical tubular part 8 is machined on its exterior surface to produce a shoulder 24 that is used to mount the angular correction lens 16. The diffusion spacer 14 is mounted inside the angular correction lens 16, between the distal end 12 of the cylindrical tubular part 8 and the angular correction lens 16. FIG. 6 shows the assembly consisting of the angular correction lens 16 and the diffusion spacer 14 to a larger scale. The angular correction lens 16 includes on the one hand a cylindrical tubular bush 26 and on the other hand an end part 28 closing the bush 26.

The dimensions of the bush 26 are adapted to the distal end of the cylindrical tubular part 8. The inside diameter of this bush corresponds to the smaller outside diameter beyond the shoulder 24 of the cylindrical tubular part 8. The bush 26 can therefore be abutted against the shoulder 24.

The end part 28 of the angular correction lens 16 has a shape depending on the required characteristics and on the shape of the distal end of the protected optical stem. Depending on the use of the endoscope, illumination may be required axially or at a given angle up to 90°. In the example shown in the drawings illumination is effected at an angle of 30°. The exterior surface of the end part 28 of the angular correction lens 16 is therefore a substantially plane surface inclined at 300 to a transverse plane. The angular correction lens 16 therefore forms a cover closing the distal end 12 of the cylindrical tubular part 8.

The angular correction lens 16 encloses the diffusion spacer 14 at the distal end of the protective sheath 4. This diffusion spacer 14 is a tubular part adapted to diffuse light guided by the cylindrical tubular part 8. When this diffusion spacer 14 is in place at the end of the protective sheath 4, it bears against the distal end 12 of the cylindrical tubular part 8, to be more precise the core of that part. It therefore has a plane annular face that comes to bear against the distal end 12 of the cylindrical tubular part 8. The opposite end of the diffusion spacer 14 is of more complex shape, depending on the intended application of the endoscope, in particular the chosen illumination angle for orienting light from the endoscope. As can be seen in FIG. 6 in particular, the distal end of the diffusion spacer 14 has substantially radial edges that define prisms 30. The interior face of the end part 28 of the angular correction lens 16 has a shape that substantially corresponds to the shape of the distal end of the diffusion spacer 14. As can be seen in FIG. 6, there is a gap between the diffusion spacer 14 and the end part 28 of the angular correction lens 16. There are only a few areas of contact between the diffusion spacer 14 and the interior face of the end part 28 of the angular correction lens 16. These areas of contact guarantee good contact between the diffusion spacer 14 and the cylindrical tubular part 8. An air lens 32 is defined in this way that also contributes to diffusing and orienting the light.

The locking system 18 at the proximal end 10 of the cylindrical tubular part 8 is known to the person skilled in the art. It is encountered as a standard feature of endoscopes. An endoscope is usually guided and supported by and locked to a guide (not shown). Here the locking system 18 is a locking system known in the art.

Similarly, the locking means 6 for fixing the protective sheath 4 to the endoscope are known to the person skilled in the art, for example locking means such as those disclosed by the document EP-0 456 761.

The sleeve support 20 connects a flexible sleeve 34 to the rigid protective sheath 4 (see FIG. 5). Here this is a flexible synthetic material sleeve. It has a length of several meters. Thus before using the protection device described here, this flexible sleeve 34 is pleated. To facilitate deployment of this sleeve over the video endoscope and supply of power to the endoscope, the sleeve is preferably pleated telescopically.

FIG. 3 is an exploded view of the handle of the video endoscope and the main components that it contains.

The housing 2 proper includes a rear body 36, a front body 38 and a front cap 40. Electricity and light are fed in through a sleeve support 42.

Inside the housing 2 is an image sensor 44 associated with a lens assembly 46 including optical lenses that are not shown.

The image sensor 44 is mounted in a support 48. Behind the image sensor 44 are printed circuits 50 incorporating electronic means for management and control of the video endoscope. A keypad 52 fixed to the rear body 36 serves as an interface between the printed circuits 50 and a user.

The video endoscope receives light from an exterior light source via the sleeve support 42. Thus light is fed to the video endoscope via optical fibers. At the support 48 they are distributed around the image sensor 44 and the lens assembly 46 and are then connected to a conical guide 54 to form an annular light output the dimensions of which substantially match those of the cross section of the cylindrical tubular part 8 of the protective sheath 4. A cylindrical tubular spacer (not shown) guides the light from the annular light output inside the housing 2 as far as the locking means 6 so that light can be transmitted from the exterior light source to the cylindrical tubular part 8 of the protective sheath 4 and then form an annular light beam around the proximal end of the rigid optical stem.

In front of the housing 2 of the video endoscope is a coupling part 56 which carries on the one hand the rigid optical stem (not shown) and on the other hand locking means complementary to the locking means 6 of the protective sheath 4. The front cap 40 contributes to locking the rigid optical stem onto the video endoscope.

A ball bearing 58 is disposed between the coupling part 56 and the front body 38 of the housing 2. It is therefore possible to turn the body of the housing 2 with the image sensor 44 relative to the rigid optical stem. A locking screw 60 is used to lock the housing 2 in a given position.

The rigid optical stem of an endoscope of the invention advantageously includes only an optical rod disposed in a tube, for example a metal tube. The optical rod conveys light from the distal part of the endoscope stem to its proximal part, whence it is directed toward the image sensor 44. The outside diameter of this endoscope stem (rod+tube) can be of the order of 2 mm (or even less).

In the assembly described above, comprising the video endoscope and its protective device, the protective sheath 4 is an active part that conducts light to illuminate the organ to be examined by means of the video endoscope and is therefore part of the endoscope. Thus here the combination of the protective sheath 4 and the flexible sleeve 34 no longer serves only to protect the patient from contamination but also plays a role in the operation of the video endoscope. Whereas in prior art endoscopes the invasive part of the endoscope, whether used with a sterile exterior sheath or not, on the one hand conveys light to the area to be examined and on the other hand films that area, here the function of the rigid stem of the endoscope is only to enable image capture by the image sensor 44. The function of conveying light to the distal part is entirely implemented by the protective sheath. The outside diameter of the rigid optical stem can therefore be small. It is therefore possible to produce endoscopes with an optical stem having a diameter of 2 mm or even less. The protective sheath 4 of a protection device of the invention can then have an outside diameter of the order of 4 mm, which corresponds to the outside diameter of the invasive part of a prior art small diameter endoscope. The invention can of course be used for other, larger or smaller, diameters.

The protection device, and in particular its protective sheath, provide good light guidance. A light source of lower power can be used, compared to prior art endoscopes. An endoscope as described above can function with a 24 W lamp whereas 250 to 300 W lamps are routinely used in prior art endoscopes.

The shape of the distal lens and the associated diffusion spacer can be adapted to produce an endoscope for all observation angles used, for example 0°, 30°, 45°, 70° and 90°.

In an endoscope of the present invention, the protection device is disposable. It can easily be fitted to and removed from the rigid optical stem of the endoscope. The rigid optical stem is reusable. Between two successive uses, the protective device is changed and the rigid optical stem can be disinfected using a disinfectant product. The down time of the endoscope between two uses is therefore very short.

Compared to prior art protective sheaths, a protective sheath 4 of the invention has a thicker wall for guiding light. This increased thickness leads to an increase in stiffness that makes the endoscope safer to use.

It follows equally from the foregoing description that the endoscope is simplified. Its cost can therefore be low.

The present invention is not limited to the embodiment described above by way of nonlimiting example. It relates equally to all variants evident to the person skilled in the art within the scope of the following claims.

The invention claimed is:

1. An endoscope protection device, comprising:
   a sheath with a rigid cylindrical tubular part; and
   an associated flexible sleeve, wherein
   the rigid cylindrical tubular part is produced from a material able to transport light,
   the rigid cylindrical tubular part is treated to guide light from a light source from a proximal end to a distal end of the rigid cylindrical tubular part, and
   the distal end of the cylindrical tubular part includes means for diffusing and/or orienting light guided by the cylindrical tubular part, wherein
   the means for diffusing and/or orienting light include a diffusion spacer and an angular correction lens, wherein
   the diffusion spacer is a tubular part having a plane transverse face adapted to rest against the distal end of the cylindrical tubular part while a face opposite to the transverse face has a number of edges, or rounded edges, to form a number of prisms, wherein
   the diffusion spacer is disposed between the angular correction lens and the distal end of the cylindrical tubular part and there is a gap between the diffusion spacer and the angular correction lens forming an air lens between those two components, wherein
   the angular correction lens is a lens having an interior face proximal to the prisms of the diffusion spacer and an exterior face opposite the interior face, and the interior face of the angular correction lens has a shape that corresponds to the shape of the prisms of the diffusion spacer.

2. The endoscope protection device according to claim 1, wherein the cylindrical tubular part (8) includes a core produced in a first material and the core of this cylindrical tubular part has interior and exterior faces coated with a material having a refractive index lower than that of the first material.

3. The endoscope protection device according to claim 2, wherein
   the material used to produce the core of the cylindrical tubular part is chosen from the group consisting of PMMA (polymethylmethacrylates) and polystyrene.

4. The endoscope protection device according to claim 2, wherein the material used to coat the core is chosen from the group consisting of PMMA (polymethylmethacrylates) and fluorinated polymers.

5. The endoscope protection device according to claim 1, wherein the outside diameter of its rigid tubular part is less than 5 mm.

* * * * *

UNITED STATES PATENT AND TRADEMARK OFFICE
CERTIFICATE OF CORRECTION

PATENT NO. : 8,454,501 B2  
APPLICATION NO. : 12/295726  
DATED : June 4, 2013  
INVENTOR(S) : Fernandez et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 998 days.

Signed and Sealed this  
Eighth Day of September, 2015

Michelle K. Lee  
*Director of the United States Patent and Trademark Office*